(12) United States Patent
Shah et al.

(10) Patent No.: US 8,568,776 B2
(45) Date of Patent: Oct. 29, 2013

(54) MULTIPARTICULATE L-MENTHOL FORMULATIONS AND RELATED METHODS

(75) Inventors: Syed M. Shah, Boca Raton, FL (US); Daniel Hassan, Boca Raton, FL (US); Sarah Hassan, Boca Raton, FL (US)

(73) Assignee: ZX Pharma, LLC, Boca Raton, FL (US)

( * ) Notice: Subject to any disclaimer, the term of this patent is extended or adjusted under 35 U.S.C. 154(b) by 0 days.

(21) Appl. No.: 13/367,747

(22) Filed: Feb. 7, 2012

(65) Prior Publication Data

US 2012/0207842 A1   Aug. 16, 2012

Related U.S. Application Data

(60) Provisional application No. 61/441,716, filed on Feb. 11, 2011, provisional application No. 61/486,523, filed on May 16, 2011.

(51) Int. Cl.
   *A61K 9/26* (2006.01)
(52) U.S. Cl.
   USPC ............ 424/469; 424/468; 424/474; 568/829
(58) Field of Classification Search
   USPC ........................ 424/468, 469, 474; 568/829
   See application file for complete search history.

(56) References Cited

U.S. PATENT DOCUMENTS

| | | | |
|---|---|---|---|
| 5,397,573 A * | 3/1995 | Kajs et al. ............... | 424/451 |
| 6,306,435 B1 | 10/2001 | Chen et al. | |
| 7,115,282 B2 | 10/2006 | Shefer et al. | |
| 7,670,624 B2 | 3/2010 | Tsutsumi et al. | |
| 7,790,755 B2 | 9/2010 | Akiyama et al. | |
| 7,803,817 B2 | 9/2010 | Kostadinov et al. | |
| 7,838,027 B2 | 11/2010 | Rao et al. | |
| 2003/0143272 A1 | 7/2003 | Waterman | |
| 2003/0207851 A1 | 11/2003 | Wei | |
| 2004/0062778 A1 | 4/2004 | Shefer et al. | |
| 2005/0069579 A1 | 3/2005 | Kamaguchi et al. | |
| 2009/0004262 A1 | 1/2009 | Shaw et al. | |
| 2011/0081451 A1 | 4/2011 | Siegel et al. | |

OTHER PUBLICATIONS

ISR, US, May 23, 2012.
Dey, et al., Multiparticulate Drug Delivery Systems for Controlled Release, Tropical Journal of Pharmaceutical Research, Sep. 2008; 7 (3): 1067-1075, Pharmacotherapy Group, Faculty of Pharmacy, University of Benin, Benin City, 300001 Nigeria.
Final Report on the Safety Assessment of Mentha Piperita (Peppermint) Oil, Mentha Piperita (Peppermint) Leaf Extract, Mentha Piperita (Peppermint) Leaf, and Mentha Piperita (Peppermint) Leaf Water, International Journal of Toxicology, 2001 20:61, online version at http://ijt.sagepub.com/content/20/3/_suppl/61.
Sibanda, et al., Experimental Design for the Formulation and Optimization of Novel Cross-Linked Oilispheres Developed for In Vitro Site-Specific Release of Mentha piperita Oil, AAPS PharmSciTech 2004; 5 (1) Article 18 (http://www.aapspharmscitech.org, Submitted Nov. 5, 2003, Accepted Feb. 18, 2004.
Pilbrant, et al., Development of an oral formulation of omeprazole, Scand J. Gastroenterol 1985; 20 (suppl 108): 113-120.
Pittler, et al., Peppermint Oil for Irritable Bowel Syndrome: A Critical Review and Metaanalysis, The American Journal of Gastroenterology, vol. 93, No. 7, 1998, 1131-1135.
Bogentoft, et al., Influence of Food on the Absorption of Acetylsalicylic Acid from Enteric-Coated Dosage Forms, European J. clin. Pharmacol, 14, 351-355, (1978).
Kline, et al., Enteric-coated, pH-dependent peppermint oil capsules for the treatment of irritable bowel syndrome in children, J Pediatr 2001; 138: 125-8.
Baranauskiene, et al, Flavor Retention of Peppermint (Mentha piperita L.) Essential Oil Spray-Dried in Modified Starches during Encapsulation and Storage, J. Agric. Food Chem, 2007, 55, 3027-3036.
Dong, et al., Effect of processing parameters on the formation of spherical multinuclear microcapsules encapsulating peppermint oil by coacervation, Journal of Microencapsulation, Nov. 2007; 24(7): 634-646.
RXMED: Pharmaceutical Information—Colpermin, Peppermint Oil Symptomatic Relief of Irritable Bowel Syndrome, Jan. 4, 2010.
Rees et al., treating irritable bowel syndrome with peppermint oil, British Medical Journal, Oct. 6, 1979.

\* cited by examiner

*Primary Examiner* — Ali Soroush
(74) *Attorney, Agent, or Firm* — Allen, Dyer, Doppelt, Milbrath & Gilchrist, P.A.

(57) ABSTRACT

Enteric coated multiparticulate formulations that use L-menthol as an active ingredient are disclosed. In one embodiment, the multiparticulate formulation comprises a plurality of particulates having a reduced release under gastric conditions and an elevated release at neutral pH. The particulates comprise a core comprising L-menthol as an active ingredient. The L-menthol is supplied to the core as an at least 80% pure L-menthol material. An enteric coating is over the core. The enteric coating is effective to release at least about 80% of the L-menthol within about two hours of being placed in a substantially neutral pH environment. Other aspects of the invention include methods of making and methods of using the multiparticulate formulations.

24 Claims, 1 Drawing Sheet

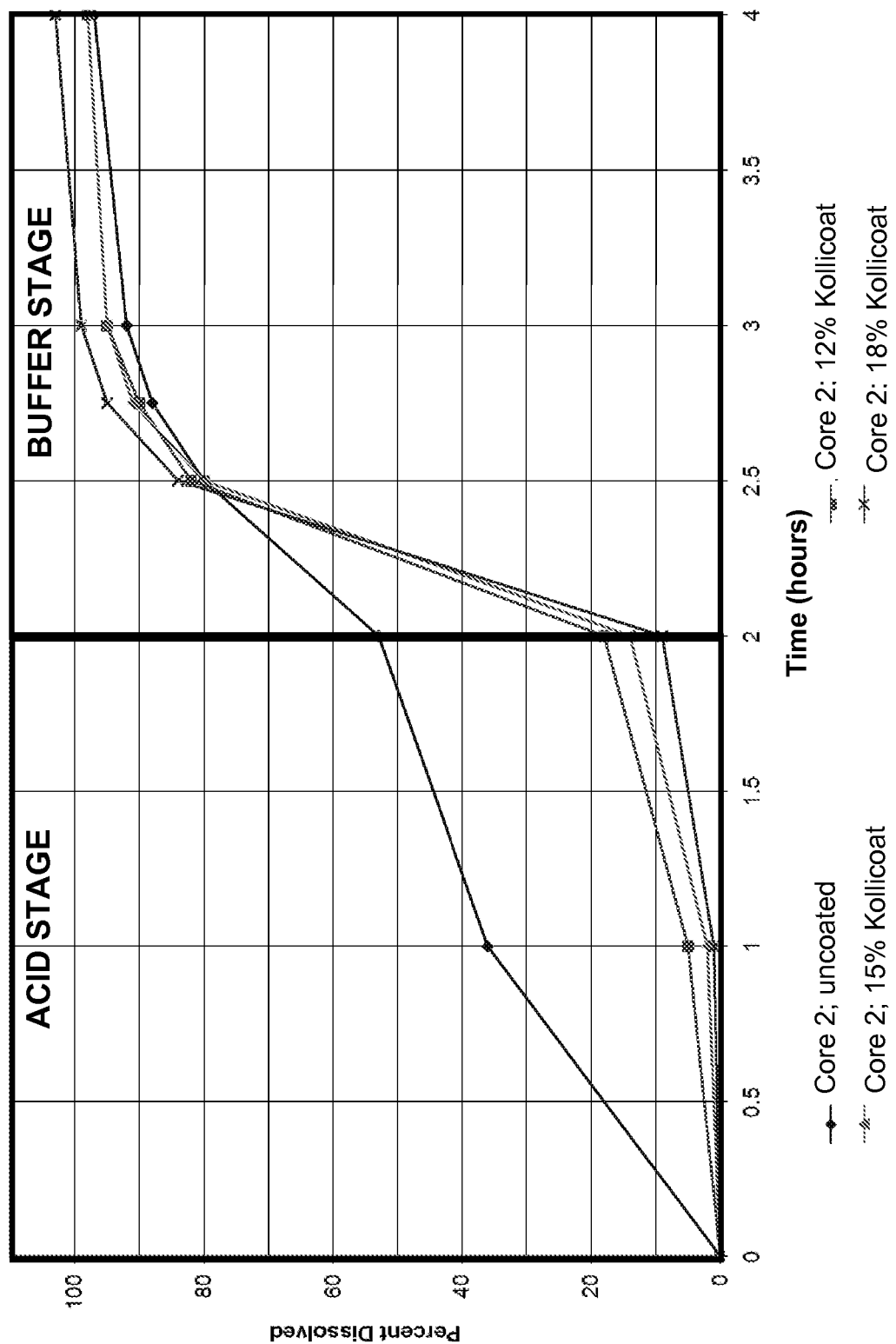

MULTIPARTICULATE L-MENTHOL FORMULATIONS AND RELATED METHODS

CROSS-REFERENCE TO RELATED APPLICATION

This application claims priority to U.S. Provisional Patent Application Ser. No. 61/441,716 filed on Feb. 11, 2011 entitled "Multiparticulate Formulations and Related Methods," the contents of which are incorporated by reference herein, and to U.S. Provisional Patent Application Ser. No. 61/486,523 filed on May 16, 2011 entitled "Multiparticulate Formulations and Related Methods," the contents of which are incorporated by reference herein in their entirety.

FIELD OF THE INVENTION

The invention relates to multiparticulate formulations for delivering high purity L-menthol to the intestines, and, more particularly, to enteric coated high purity L-menthol multiparticulate formulations and related methods.

BACKGROUND

Essential oils have been used for their bioactivity for quite some time. Some essential oils are currently being used as medicaments. For example the plants *mentha piperita* or *mentha arvensis*, are the two primary sources of peppermint oil. Peppermint oil is effective at treating the symptoms of gastrointestinal disorders such as irritable bowel syndrome (IBS). These symptoms can include pain, discomfort, bloating, constipation, and/or diarrhea. Clinical trials have demonstrated significant alleviation of the symptoms associated with IBS through the use of peppermint oil in single unit capsules coated with the cellulose acetate-phthalate enteric polymer or other enteric-coating polymers.

For maximal efficacy in the treatment of IBS and to avoid related complications, peppermint oil should be locally delivered to the intestines, while avoiding the stomach. If peppermint oil is released from its dosage form prior to passing through the pyloric sphincter into the intestines, it can irritate the mucous membranes in the digestive tract. Releasing peppermint oil directly into the stomach can cause heartburn (gastric irritation) and gastro-esophogeal reflux disease. Therefore, since peppermint oil is usually administered orally, it should preferably be prepared with an enteric coating.

Enteric-coated single unit capsules for treating irritable bowel syndrome that contain peppermint oil currently exist. But, even though the enteric coated single unit capsules are meant to delay the release of peppermint oil until after the capsule enters the intestines, this approach to treating IBS has several drawbacks. The drawbacks include premature release of the peppermint oil from the capsule in the stomach, resulting in heartburn. Also, the accidental chewing of the capsule causes the enteric coat to rupture prematurely and release the oil in the stomach. Using current formulations of peppermint oil, significant doses are required to achieve an efficacious concentration of peppermint oil in the body. For example, each of the above referenced capsules contains about 200 mg of peppermint oil and must be taken three times a day, 30-60 minutes prior to a meal. The dose can be increased to two capsules taken three times daily in some situations.

Enteric-coated peppermint oil is typically administered as a single-unit formulation. However, in a single-unit formulation, the amount of peppermint oil absorbed by the intestines can vary from dose to dose for several reasons. First, single-unit enteric capsule formulation can get attached to the esophagus because of the muco-adhesive properties of the enteric coat and therefore not enter the stomach within the desired time frame. The single unit enteric coated capsules, like enteric coated single unit tablets have been shown to not release the active ingredient from the single unit formulation because the single unit's size is too large to pass through the constriction in the stomach's pylorus valve. The enteric coat of the capsule may also prematurely crack or rupture because of the force created by the swelling of the gelatin (or hypromellose) seal coat against the thinner outer enteric coat. Peppermint oil containing capsules have a lower specific gravity than the stomach contents, and tend to float rather than settle and then pass through the pylorus constriction between the stomach and the lower intestines.

Non-disintegrating tablets or capsules given with food may stay in the stomach for long times, 10 to 15 hours, before they are emptied into the small intestine. Small particles, with diameters less than 3 mm, are emptied from the stomach more regularly, regardless of whether they are given with food. The 10 to 15 hours that an enteric coated hard gelatin or hypromellose capsule can get exposure to gastric conditions in a fed state may cause the enteric coat to rupture and the hard gelatin (or hypromellose) seal coat to dissolve, resulting in the peppermint oil being released in the stomach and causing heartburn or gastric irritation.

Even when the single unit enteric coated capsule passes through the pylorus intact in a timely fashion, when it reaches the small intestine the coating dissolves and a bolus of oil is released in the intestine. This dosage dumping, a situation in which the active ingredient is released and gives very high local exposure in a segment of the intestine, is also undesirable because it prevents uniform and steady exposure of peppermint oil in the G.I. lumen. This high local exposure to one section of the G.I. lumen may actually aggravate symptoms of IBS.

Single-unit formulations are also significantly influenced by the quantity of food in the stomach. Gastric emptying rates of single unit doses are erratic and unpredictable. Single-unit enteric-coated tablets or capsules taken with food may stay in the stomach for many hours before being emptied into the small intestine. As a result, single-unit formulations present both inter and intra-subject variability with respect to the bioavailable concentration of active ingredient. According to regulatory guidelines, enteric-coated single-unit capsules can never be bioequivalent with multiple-unit enteric-coated dosage forms. A single-unit enteric preparation containing peppermint oil was disclosed in U.S. Pat. No. 4,687,667, which is hereby incorporated by reference in its entirety except to the extent it may be inconsistent with this application.

The currently available delayed release single unit dosage forms containing enteric-coated peppermint oil have another limitation. They dump their primary active ingredient, L-menthol, when the enteric layer disintegrates. The terminal half life of L-menthol is ~1.34 hours. Therefore, the systemic exposure of L-menthol is limited to approximately 4 hours, resulting in the need for frequent (usually three times a day) to relieve the symptoms of IBS. The use of a single unit non-disintegrating delayed release dosage form is undesirable due to unpredictable absorption and longer residence time in the stomach.

SUMMARY

An aspect of the invention is to provide a L-menthol multiparticulate formulation with an enteric coating, using high-purity L-menthol.

In one embodiment, the multiparticulate formulation comprises a plurality of particulates having a reduced release under gastric conditions and an elevated release at neutral pH. The particulates comprise a core comprising L-menthol as an active ingredient. The L-menthol is supplied to the core as an at least 80% pure L-menthol material, such as a purified L-menthol containing liquid or L-menthol crystals. An enteric coating is over the core. The enteric coating is effective to release at least about 80% of the L-menthol within about two hours of being placed in a substantially neutral pH environment.

In another embodiment, the core comprises about 30% to about 70% w/w L-menthol, about 25% to about 60% w/w microcrystalline cellulose, about 0.5% to about 4% w/w hypromellose, about 1% to about 3% w/w polysorbate 80, about 2% to about 15% w/w colloidal silica, about 4% to about 6% w/w croscarmellose sodium, and about 0.5% to about 4% w/w ascorbic acid. A sub-coating comprising hypromellose is on the core. An enteric coating is on the sub-coating. Also, the particulates have an average diameter of not more than 3 mm.

The invention also provides methods of making the multiparticulate formulations. An exemplary method of making an L-menthol multiparticulate formulation of the invention comprises preparing a plurality of cores comprising crystalline L-menthol as an active ingredient, drying the cores, coating the cores with an enteric coating effective to release at least about 80% of the L-menthol within about two hours of being placed in a substantially neutral pH environment; and drying the enteric coated cores. In a particularly preferred embodiment the temperature of the cores and enteric coated cores is maintained at or below about 30° C.

These and other objects, aspects, and advantages of the present invention will be better appreciated in view of the drawings and following description of certain embodiments.

BRIEF DESCRIPTION OF THE DRAWINGS

FIG. 1 is a graph of the dissolution of various samples of multiparticulate formulations of the invention in a 0.1 HCl solution (acid stage) and subsequently a pH=6.8 buffer (buffer stage).

DETAILED DESCRIPTION OF CERTAIN EMBODIMENTS

In the Summary above and in the Detailed Description of Certain Embodiments and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, that feature can also be used, to the extent possible, in combination with and/or in the context of other particular aspects and embodiments of the invention, and in the invention generally.

The term "comprises" is used herein to mean that other ingredients, steps, etc. are optionally present. When reference is made herein to a method comprising two or more defined steps, the steps can be carried in any order or simultaneously (except where the context excludes that possibility), and the method can include one or more steps which are carried out before any of the defined steps, between two of the defined steps, or after all of the defined steps (except where the context excludes that possibility).

In this section, the present invention will be described more fully with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will convey the scope of the invention to those skilled in the art.

The efficacy of peppermint oil in controlling smooth muscle contraction can be substituted by its main bio-active constituent, L-menthol. Peppermint oil derived from *Mentha piperita* only contains up to 50% menthol and *Mentha arvensis* contains only approximately 70-80% menthol. The other components of peppermint oil include menthone, pulegone, menthofuran, and limone, which may cause undesirable side effects or diminish the effectiveness of the L-menthol. In contrast to peppermint oil, which is primarily available as a liquid, L-menthol is available in a liquid and crystalline powder form. The inventors have advantageously developed a unique combination of ingredients and processing methods for providing an enteric coated multiparticulate formulation comprising high purity liquid or solid L-menthol.

One aspect of the invention is to provide a multiparticulate formulation comprising solid L-menthol for treating gastrointestinal disorders such as gastrointestinal discomfort and irritable bowel syndrome. This is advantageous over typical peppermint oil formulations because the undesirable menthone, pulegone, menthofuran, and limone are not co-administered with L-menthol to a patient who takes the formulation, thus preventing the undesirable side effects or reduced efficacy of L-menthol that may result.

Further, because it is desirable for L-menthol to be released into the intestines as opposed to the stomach, the formulation provides a reduced release in the stomach and an elevated release at a substantially neutral pH, such as the pH found in the intestines. In a preferred embodiment, the formulation allows for release of at least about 80% of the L-menthol within about two hours of being placed in a substantially neutral pH environment. As used herein, a substantially neutral pH environment means an environment having a pH of about 7, including, but not limited to a pH of between about 6.5 to about 7.5, also including the pH environment of the intestines. In another preferred embodiment, the formulation allows for the release of no more than about 10% of the L-menthol within about 2 hours of being placed in a 0.1 N HCl solution and, subsequently, no less than about 85% of the L-menthol within about 45 minutes of being placed in a substantially neutral pH environment, which is consistent with U.S. Pat. No. 711 enteric protection specifications.

The solid L-menthol multiparticulate formulations of the invention provides an advantageous L-menthol oral delivery vehicle that can be administered to a patient. A multiparticulate formulation of the invention comprise a plurality of individual particulates that are preferably spheroidal in shape and are preferably configured for incorporation into a capsule or packet-type oral delivery dosage form.

The invention also provides a unique method of making the multiparticulate formulations in which the temperature of the formation process is controlled and the enteric coating material chosen to prevent L-menthol from significantly volatilizing or degrading, thereby allowing the formulation of the invention to comprise L-menthol supplied from a high purity L-menthol source such as a purified liquid L-menthol or solid L-menthol preferably at or above 80% purity.

The data provided in the examples section show that the inventors have successfully produced a high purity enteric coated multiparticulate L-menthol composition with a dissolution profile consistent with U.S. Pat. No. 711 specifications. This formulation allows for prolonged duration of action, more reliable dosing, and reduced drawbacks from the undesirable L-menthol derivatives or degradants when compared to current marketed peppermint oil formulations.

The multiparticulates of the invention comprise a plurality of particulates which are preferably spheroidal in shape. Each particulate is sized to fit through the pyloric sphincter in a relaxed state. The diameter of the particulates is preferably in the range of about 0.1-3 mm, more preferably about 1-2.5 mm.

The particulates are comprised of a preferably spheroidal core with an enteric coating over the core. The particulates may also have an optional sub-coating between the core and enteric coating. In a preferred embodiment, the sub-coating comprises hydroxypropyl methyl cellulose, also known as "HPMC" or "hypromellose." The particulates may also include one or more additional coatings such as a sealant coating or a color coating on the enteric coating. In a preferred embodiment, the sub-coating is hypromellose E5. The sub-coating is preferably between about 1-5% w/w of the enteric coated particulate.

The core comprises the primary active ingredient, which is high purity L-menthol such as solid L-menthol. Solid L-menthol is a crystalline material at room temperature, has a melting point at standard pressure of about 42°-45° C., and may undergo sublimation at slightly above room temperature. The core may also comprise an antioxidant, which can maintain the purity of the L-menthol to prevent the L-menthol from oxidizing into undesirable derivatives. Examples of antioxidants include, but are not limited to tocopherol (vitamin E,) BHT (butylated hydroxy toluene), BHA (butylayted hydroxy anisole), and ascorbic acid. The core may also comprise one or more inactive ingredients.

The term "solid L-menthol" means L-menthol in its solid form, preferably in its crystalline form. In the crystalline form, L-menthol is substantially free of undesirable impurities. Although it may not always be necessary, it is preferred that the starting material for L-menthol appear as visually perceptible L-menthol crystals that are then ground into a polycrystalline powder. During development of the formulation of the invention, the inventors found that micronizing the L-menthol produced good results. Although not intending to be bound by theory, it is believed that micronizing the L-menthol produces more L-menthol surface area, which improves L-menthol's aqueous solubility. It is preferred, however, that the L-menthol be micronized without raising the temperature of the L-menthol enough to degrade the L-menthol molecules, cause L-menthol to melt, or cause L-menthol to undergo sublimation. A suitable technique for producing micronized L-menthol crystals involves jet milling. A preferred concentration of L-menthol in the core is between about 30% to 70% w/w of the total enteric coated particulate.

The core may also include one or more of filler, stabilizer, binder, surfactant, processing aid, or disintegrant. By way of example only, suitable materials for performing these functions are provided. A suitable filler includes a pharmaceutically suitable filler. In one embodiment, the filler is microcrystalline cellulose. A suitable binder includes a pharmaceutically suitable binder. In a preferred embodiment, the binder is a cellulosic water soluble polymer such as cellulose ether. Because L-menthol is not highly soluble in water, it may be advantageous to include a surfactant as a solubilizing agent. A preferred solubulizing agent is polysorbate 80 or sodium lauryl sulfate ("SLS"). It was discovered that the solubilizing agent improved the wettability and, therefore, the rate and extent of release of L-menthol from the particulates. Polysorbate 80 also enhances absorption of L-menthol into the plasma. A suitable processing aid includes a pharmaceutically suitable processing aid such as for improving the flowability of the core materials during processing. In a preferred embodiment, the processing aid is colloidal silicon dioxide. A suitable disintegrant includes a pharmaceutically suitable disintegrant. In a preferred embodiment, the disintegrant is croscarmellose sodium.

A preferred composition for the core comprises about: 30-70% w/w micronized L-menthol; about 2% to 15% w/w processing aid; about 25 to 60% w/w filler; about 4% to 6% w/w disintegrant; about 0.5% to 4% w/w binder; about 1% to 3% w/w solubilizing agent; and about 0.5% to 4% w/w antioxidant. Here the % w/w is relative to the total weight of the enteric coated particulate.

A listing of ingredients for two exemplary embodiments of the core is shown in Table 1. In Table 1, the % w/w is based on the uncoated core. For Core 1, L-Menthol was supplied as 95% w/w L-Menthol/5% w/w Cab-O-Sil M5P (Silicon Dioxide) and was milled using Fitz Mill equipment. For Core 2, L-Menthol was supplied as 95% w/w L-Menthol/5% w/w Cab-O-Sil M5P (Silicon Dioxide) and was milled using Jet Pulverizer equipment. The % represents the theoretical quantity of L-Menthol in the blend. Core 1 used used Avicel Ph101 as the filler and Core 2 used Avicel Ph 102 as the filler. These are chemically identical and vary only by particle size.

The enteric coating is applied over the uncoated core or, if the sub-coating is present, over the sub-coating. The enteric coating is preferably applied so that it comprises about 5-35% w/w of the enteric coated particulate. A preferred enteric coating material is a methacrylic acid based material such as a methacrylic acid based co-polymer. Examples of suitable methacrylic acid based copolymers include Eudragit L30D-55 or Kollicoat MAE 30 DP. These materials may be combined with other materials such as plasticizers for forming an enteric coating solution. In a typical embodiment, an enteric coating solution comprises about 20-40% w/w water, about 0.5-1.5% w/w plasticizer, about 5-15% anti-adherent, and about 40-70% copolymer. By way of example only, a suitable plasticizer is triethyl citrate and a suitable anti-adherent is PlasACRYL T20.

Although it may not always be necessary, it is preferred that the enteric coating material be applied to the core without heating the core above about 30° C. This can be particularly difficult considering that enteric coatings are typically applied in a fluidized bed coater at sufficient air inlet temperature to result in a product temperature of about 38-42° C. Unfortunately, at such a high temperature, L-menthol tends to degrade and volatilize. This made it very difficult to produce a high purity, solid L-menthol formulation that met or approximated the desired U.S. Pat. No. 711 enteric specifications. The inventors found that both Eudragit L30D-55 and Kollicoat MAE 30 DP were suitable because they could be reliably applied to the cores at lower temperatures with good coalescence between the enteric coating and the underlying material. Without intending to be bound by theory, this may be because the glass transition temperature $T_g$ of these methacrylic acid based copolymers is roughly about 26° C. and depends on the plasticizer used. These methacrylic acid copolymer based enteric coating materials do not require pH sensitive pore formers to dissolve at or near neutral pH.

A listing of the ingredients in an exemplary embodiment of enteric coated particulates is provided in Table 2. The core in this example is Core 2. The % w/w is based on the weight enteric coated particulate.

Methods of making the multiparticulate formulations in accordance with another aspect of the invention will now be described. The core is typically prepared by wet granulating the core materials into a wet mass, extruding the wet mass to form an extrudate, cutting the extrudate into a plurality of core pieces, and spheronizing the core pieces. If the antioxidant is in a liquid solution, the liquid antioxidant solution may be sprayed into the wet mass. The spheronized core pieces are preferably dried to <3% based on the Karl Fischer method. The spheronized core pieces are then coated with the enteric coating material. The enteric coating is typically applied in a fluidized bed coater. The enteric coated particulates are subsequently dried, to <3% (Karl Fischer). The dried enteric coated multiparticulates may then be prepared into a suitable pharmaceutical dosage form such as a capsule or tablet, for example. A typical preferred capsule contains about 250 mg of the particulates. Depending on the desired dosage, however, this may be adjusted.

The inventors found that L-menthol may sublimate, oxidize, or otherwise degrade during processing if the processing parameters are not carefully controlled. For example, the mechanical force of granulating the L-menthol may cause it to heat, thereby resulting in sublimation, oxidation, and/or degradation. However, using a technique for granulating the L-menthol, such as jet milling, allowed for the inventors to produce cores in which the integrity and amount of raw L-menthol was retained. Aside from issues related to granulation, drying the core pieces and applying the enteric coating can adversely heat the L-menthol as well. It is preferred that throughout the process, the temperature of the formulation be maintained at or below 30° C. and, more preferably, at or below 25° C.

The multiparticulate formulations of the invention are preferably formulated to be taken orally by a human or animal patient and to ensure that the patient receives an effective amount of high purity L-menthol over the course of several hours after ingestion. An effective amount is an amount that is sufficient to affect a disease or process in the body. In a preferred embodiment a dose of a multiparticulate formulation provides about 10 mg to 200 mg or, more preferably, about 90-110 mg of L-menthol. Doses of the multiparticulate formulation may be administered sporadically when needed for treating acute inflammations of the G.I. tract or may be administered as part of a long term regimen for treating irritable bowel syndrome. A patient may be a human or animal patient.

Accordingly, another aspect of the invention is to provide a method of treating a gastrointestinal disorder, the method comprising administering a multiparticulate formulation of the invention to the patient (human or animal).

EXAMPLES

This section describes examples of certain preferred embodiments of the invention. The examples are not intended to limit the scope of the invention in any way.

Example 1

Preparation of Multiparticulate Formulations

Experimental Details.

The equipment utilized to create the formulations herein includes the following: top loading balances, hand screens (12, 14, 16, 18, Pan, 70 mesh), Rotap sieve shaker, IKA mixer, KitchenAid food processor (pre-milling), Fitz mill equipped with a 0.065" screen, Jet Mill, Key International high sheer mixer, Glatt GPCC-3 fluid bed drier, Glatt GPCC-3 fluid bed dried with 7" Wurster, Karl Fischer moisture analyzer, and a spheronizer.

Preparation of Core 1.

Core 1, shown in Table 1, was prepared as described above utilizing the following settings. The wet granulation settings were: impeller speed 300 rpm, chopper speed 3450 rpm, wet massing time 80-90 seconds, maximum Impeller Power 5.5-6.2 amps. The extrusion settings were: impeller speed 25 rpm, feeder speed 30 rpm, screen size 1.2 mm. Extrudates were charged to a spheronizer rotating at 500 rpm. Core 1 particulates were dried at 17-23° C. at 45 cfm air flow for 60-75 minutes.

Preparation of Core 2.

Core 2, shown in Table 1, was prepared as described above utilizing the following settings: The wet granulation setting were: impeller speed 640 rpm, chopper speed 9450 rpm, maximum impeller power 6-7 amps. The extrusion settings were: impeller speed 25 rpm, feeder speed rpm, screen size 1.2 mm. Extrudates were charged to a spheronizer rotating at 900-925 rpm. Core 2 particulates were dried at 17-23° C. at 45 cfm air flow for 60-75 minutes.

Application of Sub-Coating.

Core 1 and Core 2 particulates were separated based on their size. The fraction that fell within the 14-18 mesh size were chosen for sub-coating. The cores were placed into a fluidized bed dryer and the sub-coating was sprayed onto the cores in the form of a 10% hypromellose (hypromellose E5) aqueous solution that was at room temperature.

Preparation of enteric coating solutions. Two of the enteric coatings that were evaluated individually comprised Eudragit L30D-55 and Kollicoat MAE 30 DP. The enteric coatings were applied to the cores in a fluidized bed coater (7" wurster) as a liquid solution. Tables 3 and 4 show the ingredients used in the Eudragit coating (enteric coating solution A) and the Kollicoat coating (enteric coating solution B), respectively.

Enteric coating solution A was applied to the cores using the following parameters: the inlet temperature was maintained between 22.7° C. and 23° C.; the exhaust temperature was maintained between 27° C. and 30° C.; the air flow was maintained between 20 and 22 cfm; the spray rate was maintained between 4.15 and 4.4 g/min; the product temperature was maintained between 19° C. and 22° C.

Enteric coating solution B was applied to the cores using the following parameters: the inlet temperature was maintained between 22.7° C. and 23° C.; the exhaust temperature was maintained between 28° C. and 30° C.; the air flow was maintained between 20 and 22 cfm; the spray rate was maintained at about 4.25 g/min; and the product temperature was maintained between 19° C. and 22° C.

Example 2

Evaluation of Prepared Multiparticulate Formulations

The prepared multiparticulate formulations were evaluated to determine whether they met or approximated the desired U.S. Pat. No. 711 enteric specifications. To meet U.S. Pat. No. 711 enteric specifications, less than 10% of the active ingredient should be released in 2 hours in a 0.1 N HCl solution ("acid stage"). Subsequently, no less than 85% of the active ingredient should be released in 45 minutes in a pH 6.8 buffer ("buffer stage").

The data in Tables 5 and 6 confirm that both the Eudragit and Kollicoat coatings can successfully be used with crystalline L-menthol to form enteric coated L-menthol multiparticulate formulations that meet or approximate U.S. Pat. No. 711 enteric specifications. In Tables 5 and 6, the batch identification refers to the core used, the coating on the core, and the preparation number for the specific formulation. A 3% w/w hypromellose sub-coating was applied to all of the cores before they were coated with the specified enteric coating.

In the acid stage, the samples were placed into a 0.1 N HCl solution for two hours. The samples were subsequently removed from the acid stage and placed in the buffer stage for the number of hours specified. The numbers indicate the % L-menthol released at the specified number of hours.

FIG. 1 is a graph of the dissolution profile for several of the multiparticulate formulations comprising cores coated with Kollicoat. The % w/w of Kollicoat relative to the weight of the particulate was varied to determine which % provides the most preferred results. FIG. 1 very clearly shows that the dissolution profile of the enteric coated particulates is much improved relative to the uncoated cores. The data for the enteric coated multiparticulates is approximately sigmoidal in shape with a slow increase within the first two hours in the acid stage and abrupt increase after two hours once the buffer stage begins. When the Kollicoat enteric coating is about 18% w/w of the of the weight of the particulate, less than 10 of the L-menthol is released in the acid stage and nearly 100% of the L-menthol is released within 2 hours in the buffer stage.

The present invention has been described above with reference to the accompanying drawings, in which preferred embodiments of the invention are shown. Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described. The skilled should understand that the methods and materials used and described are examples and may not be the only ones suitable for use in the invention.

Any publications, patent applications, patents, and other references mentioned herein are incorporated by reference in their entirety as if they were part of this specification. However, in case of conflict, the present specification, including any definitions, will control.

In the specification set forth above there have been disclosed typical preferred embodiments of the invention, and although specific terms are employed, the terms are used in a descriptive sense only and not for purposes of limitation. The invention has been described in some detail, but it will be apparent that various modifications and changes can be made within the spirit and scope of the invention as described in the foregoing specification and as defined in the appended claims.

TABLE 1

Ingredients of two exemplary embodiments of the core.

| Ingredient | Core 1 (grams/ % w/w) | Core 2 (grams/ % w/w) | Ingredient Function |
|---|---|---|---|
| L-Menthol | 249.6/49.92 | 241.92/48.38 | Active ingredient |
| Cab-O-Sil M5P (Colloidal Silicon Dioxide) | 10.4/2.08 | 26.88/5.38 | Processing Aid |
| Avicel (Micro Crystalline cellulose) | 190.00/38.00 | 176.20/35.24 | Filler |

TABLE 1-continued

Ingredients of two exemplary embodiments of the core.

| Ingredient | Core 1 (grams/ % w/w) | Core 2 (grams/ % w/w) | Ingredient Function |
|---|---|---|---|
| Ac-Di-Sol (Croscarmellose Sodium) | 30.00/6.00 | 30.00/6.00 | Disintegrant |
| Hypromellose (Methocel A15 Premium) | 10.00/1.00 | 10.00/1.00 | Binder |
| Polysorbate 80 | 5.00/2.00 | 10.00/2.00 | Solubilizing Agent |
| Ascorbic Acid | 5.00/1.00 | 5.00/1.00 | Antioxidant |
| Water (% of dry mass) | (93.00%) | (86.16%) | |

TABLE 2

Ingredients of an exemplary embodiment of enteric-coated particulates.

| Ingredient | Ingredient % w/w in Finished EC Multiparticulate | Ingredient Weight in Finished Dosage Form (mg) | Ingredient Function |
|---|---|---|---|
| L-Menthol | 43.816 | 100.000 | Active ingredient |
| Cab-O-Sil M5P (Colloidal Silicon Dioxide) | 2.804 | 6.399 | Processing aid |
| Avicel pH 102 | 30.234 | 69.001 | Filler |
| Ac-Di-Sol (FMC; Croscarmellose Sodium) | 5.148 | 11.748 | Disintegrant |
| Methocel A15 Premium | 1.716 | 3.916 | Binder |
| Polysorbate 80 | 0.858 | 1.958 | Solubilizing agent |
| Ascorbic Acid | 0.858 | 1.958 | Antioxidant |
| Hypromellose E5 | 2.627 | 5.995 | Sub-coating |
| Kollicoat MAE 30 DP Solids | 10.369 | 23.666 | Source of methacrylic copolymer |
| Triethyl Citrate | 0.538 | 1.227 | Plasticizer |
| PlasACRYL T20 | 1.033 | 2.358 | Anti-Adherent |
| Water[1] | | | |

[1]Evaporates

TABLE 3

Enteric Coating Solution A: Eudragit L30D-55 (Evonik)

| Ingredient | grams |
|---|---|
| Eudragit L30D-55 (30% w/w solids) | 578.7 |
| Triethyl Citrate | 9 |
| PlasACRYL T20 | 86.5 |
| Water* | 325.8 |

*Evaporates

TABLE 4

Enteric Coating Solution B: Kollicoat MAE 30 DP (BASF)

| Ingredient | grams |
|---|---|
| Kollicoat 30 DP 55 (30% w/w solids) | 578.7 |
| Triethyl Citrate | 9 |
| PlasACRYL T20 | 86.5 |
| Water* | 325.8 |

*Evaporates

TABLE 5

Dissolution Results for various Eudragit coated and uncoated multiparticulate formulations.

| | % Dissolved per Hour | | | | | | | | | |
|---|---|---|---|---|---|---|---|---|---|---|
| | Acid Stage 0.1N HCl | | Buffer Stage pH = 6.8 buffer Time (hr) | | | | | | | |
| Batch Identification | 1 | 2 | 2.25 | 2.5 | 2.75 | 3 | 4 | 6 | 8 | 10 |
| Uncoated Core 1; Preparation 1 | 49 | 52 | 149 | 105 | 101 | 99 | 97 | 95 | 94 | 92 |
| Uncoated Core 1; Preparation 2 | 34 | 41 | 72 | 77 | 77 | 76 | 75 | 75 | 75 | 74 |
| Core 1; Evonik Eudragit L30D (12% w/w) + 0.5% SLS | 2 | 5 | 35 | 65 | 77 | 80 | 86 | 85 | 85 | 84 |
| Core 1; Evonik Eudragit L30D (12% w/w) + 1.0% SLS | 2 | 5 | 42 | 73 | 83 | 88 | 91 | 90 | 90 | 89 |

TABLE 6

Dissolution Results for various Kollicoat coated and uncoated multiparticulate formulations.

| | % Dissolved per Hour | | | | | | |
|---|---|---|---|---|---|---|---|
| | Acid Stage 0.1N HCl | | Buffer Stage pH = 6.8 buffer Time (hr) | | | | |
| Batch Identification | 1 | 2 | 2.25 | 2.5 | 2.75 | 3 | 4 |
| Uncoated Core 2; Preparation 1 | 32 | 46 | | 80 | 89 | 93 | 96 |
| Uncoated Core 2; Preparation 2 | 33 | 47 | | 76 | 86 | 91 | 95 |
| Uncoated Core 2; Preparation 3 | 31 | 46 | | 75 | 86 | 91 | 95 |
| Core 2; Kollicoat MAE 30 DP (12% w/w); Preparation 1 | 5 | 16 | | 72 | 82 | 86 | 93 |
| Core 2; Kollicoat MAE 30 DP (12% w/w); Preparation 2 | 5 | 15 | | 73 | 82 | 86 | 92 |
| Core 2; Kollicoat MAE 30 DP (12% w/w); Preparation 3 | 5 | 15 | | 75 | 82 | 86 | 91 |
| Uncoated Core 2; Preparation 4 | 36 | 53 | | 80 | 88 | 92 | 97 |
| Core 2; Kollicoat MAE 30 DP (12% w/w); Preparation 4 | 5 | 18 | | 82 | 90 | 95 | 98 |
| Core 2; Kollicoat MAE 30 DP (15% w/w); Preparation 1 | 2 | 14 | | 80 | 91 | 95 | 98 |
| Core 2; Kollicoat MAE 30 DP (18% w/w); Preparation 1 | 1 | 9 | | 84 | 95 | 99 | 103 |

That which is claimed is:

1. An L-menthol multiparticulate formulation comprising a plurality of particulates having a reduced release under gastric conditions and an elevated release at neutral pH, wherein the particulates comprise:
   a core comprising L-menthol as an active ingredient, the L-menthol being supplied to the core as an at least 80% pure L-menthol material;
   an enteric coating over the core, the enteric coating being effective to release at least about 80% of the L-menthol within about two hours of being placed in a substantially neutral pH environment.

2. The multiparticulate formulation of claim 1, wherein the L-menthol is crystalline.

3. The multiparticulate formulation of claim 2, wherein the crystalline L-menthol is present as micronized particles.

4. The multiparticulate formulation of claim 1, wherein the core further comprises a solubilizing agent effective for solubilizing L-menthol.

5. The multiparticulate formulation of claim 1, wherein the core further comprises an antioxidant effective for preventing the L-menthol from oxidizing.

6. The multiparticulate formulation of claim 5, wherein the antioxidant is ascorbic acid.

7. The multiparticulate formulation of claim 1, wherein the core comprises about 30% to about 70% w/w L-menthol.

8. The multiparticulate formulation of claim 1, wherein the enteric coating comprises a polymeric material having a glass transition temperature $T_g$ of at most about 30° C.

9. The multiparticulate formulation of claim 1, wherein the enteric coating comprises a methacrylic acid based copolymer.

10. The multiparticulate formulation of claim 1, wherein the enteric coating is effective to release no more than about 10% of the L-menthol within about 2 hours of being placed in a 0.1 N HCl solution and, subsequently, no less than about 85% of the L-menthol within about 45 minutes of being placed in a substantially neutral pH environment.

11. The multiparticulate formulation of claim 1, wherein the multiparticulate formulation is present in a pharmaceutical dosage form that can be orally administered to a patient.

12. A multiparticulate composition comprising a plurality of spheroidal particulates, the particulates comprising:
   a core comprising about 30% to about 70% w/w L-menthol, the L-menthol being supplied to the core as an at least 80% pure L-menthol containing material, the core further comprising about 25% to about 60% w/w microcrystalline cellulose, about 0.5% to about 4% w/w hypromellose, about 1% to about 3% w/w polysorbate 80, about 2% to about 15% w/w colloidal silica, about 4% to about 6% w/w croscarmellose sodium, and about 0.5% to about 4% w/w ascorbic acid;
   a sub-coating comprising hypromellose on the core;
   an enteric coating on the sub-coating; and wherein the particulates have an average diameter of not more than 3 mm.

13. The multiparticulate composition of claim 12, wherein the L-menthol is crystalline.

14. The multiparticulate composition of claim 13, wherein the L-menthol is micronized.

15. The multiparticulate composition of claim 12, wherein the L-menthol is present in the amount of about 50% w/w.

16. The multiparticulate composition of claim 12, wherein the sub-coating is present in the amount of about 1% to about 5% w/w.

17. The multiparticulate composition of claim 12, wherein the enteric coating is present in the amount of about 10% to about 35% w/w.

18. The multiparticulate composition of claim 12, wherein the enteric coating comprises a methacrylic acid based copolymer.

19. The multiparticulate composition of claim 12, wherein the enteric coating is effective to release at least about 80% of the L-menthol within about two hours of being placed in a substantially neutral pH environment.

20. A method of making an L-menthol multiparticulate formulation comprising a plurality of particulates having a reduced release under gastric conditions and an elevated release at neutral pH, the method comprising:
    preparing a plurality of cores comprising crystalline L-menthol as an active ingredient;
    drying the cores;
    coating the cores with an enteric coating effective to release at least about 80% of the L-menthol within about two hours of being placed in a substantially neutral pH environment; and
    drying the enteric coated cores.

21. The method of claim 20, further comprising maintaining a temperature of the cores and enteric coated cores at or below 30° C.

22. The method of claim 21, wherein the temperature is between about 19° C. and about 22° C.

23. The method of claim 20, further comprising placing the particulates into a dosage form that can be administered orally to a patient.

24. A method of treating a gastrointestinal disorder, the method comprising administering the multiparticulate formulation of claim 1 to a patient.

* * * * *